US009149561B2

(12) United States Patent
Rizk et al.

(10) Patent No.: US 9,149,561 B2
(45) Date of Patent: Oct. 6, 2015

(54) INJECTION MOLDING OF POLY-4-HYDROXYBUTYRATE

(71) Applicant: Tepha, Inc., Lexington, MA (US)

(72) Inventors: Said Rizk, Windham, NH (US); Dennis W. Connelly, Arlington, MA (US); Matthew Bernasconi, Norwood, MA (US); Andrew J. Carter, Stow, MA (US); David P. Martin, Arlington, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 162 days.

(21) Appl. No.: 13/800,853

(22) Filed: Mar. 13, 2013

(65) Prior Publication Data
US 2013/0309166 A1 Nov. 21, 2013

Related U.S. Application Data

(60) Provisional application No. 61/713,139, filed on Oct. 12, 2012, provisional application No. 61/649,506, filed on May 21, 2012.

(51) Int. Cl.
| | | |
|---|---|---|
| A61K 47/30 | (2006.01) |
| A61L 27/18 | (2006.01) |
| C08G 63/06 | (2006.01) |
| B29C 45/00 | (2006.01) |
| A61L 31/12 | (2006.01) |
| A61L 27/44 | (2006.01) |
| A61L 27/46 | (2006.01) |
| A61L 27/58 | (2006.01) |
| A61L 31/14 | (2006.01) |

(52) U.S. Cl.
CPC .............. *A61L 27/18* (2013.01); *A61L 27/446* (2013.01); *A61L 27/46* (2013.01); *A61L 27/58* (2013.01); *A61L 31/127* (2013.01); *A61L 31/128* (2013.01); *A61L 31/148* (2013.01); *B29C 45/0055* (2013.01); *C08G 63/06* (2013.01)

(58) Field of Classification Search
None
See application file for complete search history.

(56) References Cited

U.S. PATENT DOCUMENTS

| 5,061,743 | A | 10/1991 | Herring |
| 5,811,272 | A | 9/1998 | Snell |
| 6,245,537 | B1 | 6/2001 | Williams |
| 6,316,262 | B1 | 11/2001 | Huisman |
| 6,323,010 | B1 | 11/2001 | Skraly |
| 6,548,569 | B1 | 4/2003 | Williams |
| 6,623,748 | B2 | 9/2003 | Clokie |
| 6,767,247 | B2 | 7/2004 | Rodrigues |
| 6,838,493 | B2 | 1/2005 | Williams |
| 7,179,883 | B2 | 2/2007 | Williams |
| 7,244,442 | B2 | 7/2007 | Williams |
| 7,268,205 | B2 | 9/2007 | Williams |
| 7,553,923 | B2 | 6/2009 | Williams |
| 7,618,448 | B2 | 11/2009 | Schmitz |
| 7,641,825 | B2 | 1/2010 | Rizk |
| 8,039,237 | B2 | 10/2011 | Martin |
| 8,231,889 | B2 | 7/2012 | Williams |

FOREIGN PATENT DOCUMENTS

| WO | 9851812 | 1/1998 |
| WO | 9932536 | 7/1999 |
| WO | 0056376 | 9/2000 |
| WO | 2005007195 | 1/2005 |
| WO | 2007092417 | 8/2007 |
| WO | 2007092418 | 8/2007 |
| WO | 2009085823 | 7/2009 |
| WO | 2012064526 | 5/2012 |

OTHER PUBLICATIONS

Hori, et al., "Chemical synthesis of high molecular weight poly(3-hydroxybutyrate-co-4-hydroxybutyrat e)", Polymer, 36:4703-5 (1995).
Houk, et al., "Why delta-valerolactone polymerizes and gamma-butyrolactone does not" . J. Org. Chem., 73 (7):2674-8 (2008).
Moore, et al., "Chemosynthesis of bioresorbable poly(gamma-butyrolactone) by ring-opening polymerisation: a review" , Biomaterials, 26:3771-82 (2005).

*Primary Examiner* — Hasan Ahmed
(74) *Attorney, Agent, or Firm* — Pabst Patent Group LLP

(57) ABSTRACT

Compositions of P4HB and processes to injection mold these compositions have been developed. These compositions are prepared from P4HB polymers and blends having intrinsic viscosities less than 3.2 dl/g but greater than 0.8 dl/g, moisture contents of less than 0.5% by weight, and more preferably less than 0.05% by weight, and using a polymer melt temperature during molding of at least 150° C. A preferred embodiment comprises a P4HB molding with an intrinsic viscosity of less than 3.2 dl/g that degrades rapidly in vivo.

14 Claims, 1 Drawing Sheet

Chemical structure of P4HB
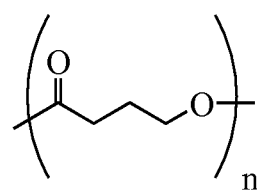

INJECTION MOLDING OF POLY-4-HYDROXYBUTYRATE

CROSS REFERENCE TO RELATED APPLICATIONS

This application claims benefit of U.S. Provisional Application No. 61/713,139 filed Oct. 12, 2012, and 61/649,506, filed May 21, 2012, both of which are herein incorporated by reference in their entirety.

FIELD OF THE INVENTION

The present invention generally relates to injection moldings of poly-4-hydroxybutyrate, the compositions used to produce these moldings, and the processes used to produce these moldings. The moldings can be used in many types of implant applications including orthopedic, craniomaxillofacial, dental, and cardiovascular, as well as in cardiology, plastic and reconstructive surgery, general surgery, ear, nose and throat surgery, and oral surgery.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure as shown in FIG. 1.

The polymer belongs to a larger class of materials called polyhydroxyalkanoates (PHAs) that are produced by numerous microorganisms (see, for example, Steinbüchel., et al., *FEMS Microbial. Lett.* 128:219-228 (1995)). In nature these polyesters are produced as storage granules inside cells, and serve to regulate energy metabolism. They are also of commercial interest because of their thermoplastic properties, biodegradability and relative ease of production.

Chemical synthesis of P4HB has been attempted, but it has been impossible to produce the polymer with a sufficiently high molecular weight that is necessary for most applications (see Hori, Y., et al., *Polymer* 36:4703-4705 (1995); Houk, et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, et al., *Biomaterials* 26:3771-3782 (2005)).

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), and by Martin, et al., *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering. U.S. Pat. Nos. 8,034,270, 8,016,883, 8,287,909, WO 2011/119742 and WO 2011/159784 disclose fibers, non-wovens, and textiles made by melt extrusion of P4HB.

Several patent applications including WO 98/51812 to Williams, WO 99/32536 to Martin, WO 00/56376 to Williams mention that PHAs may be injection molded. Certain patents describe injection molding of PHAs containing 3-hydroxyacids, including the homopolymer, poly-3-hydroxybutyrate (P3HB also known as PHB), and copolymers of 3-hydroxybutyrate with 3-hydroxyvalerate (PHBV) and copolymers with 4-hydroxybutyrate. Notably, U.S. Pat. No. 5,061,743 to Herring discloses the difficulties in processing PHAs containing 3-hydroxyacids, such as PHB and PHBV, due to their low crystallization rates, and the need to reduce cycle times. PHB also has a very narrow thermal processing window that can result in thermal decomposition of the polymer processed at elevated temperatures. Herring accordingly discloses additives such as organophosphonic acids and metal oxides to enable the injection molding of PHAs containing 3-hydroxyacids. Notably, Herring and others do not disclose how to injection mold P4HB, or how P4HB could be injection molded without additives. Moreover, since PHB and P4HB have entirely different physical and chemical properties, disclosures describing conditions to injection mold PHB do not teach how to injection mold P4HB. For example, PHB has a melt temperature of 180° C., and therefore a different thermal profile is necessary to injection mold P4HB, which has a melt temperature of just 60° C. PHB and P4HB also do not share the same molecular structure, and therefore have different crystallization rates, and whereas PHB is a relatively brittle material, P4HB is a strong pliable and tough thermoplastic.

WO 2005/007195 to Hasirci discloses a solution method to mold rods of P4HB, but does not disclose injection molded rods of P4HB. WO 2007/092418 to Schmitz discloses blends of P4HB with PLLA, and mentions that these blends may be injection molded to make tubes for stent application. In this invention, the P4HB is used to toughen PLLA. Schmitz does not disclose injection molding of P4HB or conditions to injection mold blends of P4HB with PLLA (poly-L-lactic acid). WO 2007/092417 to Rizk also discloses blends of P4HB with PLLA, wherein the P4HB is used to toughen PLLA, but does not disclose conditions to injection mold these blends or the P4HB homopolymer.

Thus, there is no disclosure of how P4HB can be injection molded, the intrinsic viscosities of P4HB that can be processed by injection molding, the loss of intrinsic viscosity upon injection molding P4HB, the conditions necessary to injection mold P4HB, the properties of P4HB moldings, such as tensile strength, elongation to break, bending strength, and tensile modulus, produced by injection molding, or the benefits of injection molding P4HB.

It is therefore an object of the present invention to provide compositions of P4HB that can be injection molded.

It is another object of the present invention to provide a means of injection molding P4HB.

It is a further object of the present invention to provide moldings of P4HB produced by injection molding characterized by specific physical properties.

It is still another object of the present invention to provide moldings of P4HB produced by injection molding with enhanced mechanical properties and controlled degradation profiles that can be used in medical applications.

SUMMARY OF THE INVENTION

Compositions of P4HB and processes to injection mold these compositions have been developed. These compositions are prepared from P4HB polymers and blends having intrinsic viscosities less than 3.2 dl/g but greater than 0.8 dl/g, moisture contents of less than 0.5% by weight, and more preferably less than 0.05% by weight, and using a polymer melt temperature during molding of at least 150° C. A preferred embodiment comprises a P4HB molding with an intrinsic viscosity of less than 3.2 dl/g that degrades rapidly in vivo. In a preferred embodiment, the polymer or blend to be injection molded is dried such that the moisture content of the polymer or blend is no greater than 0.5% by weight as measured gravimetrically, and more preferably no greater than 0.05% by weight.

The P4HB polymer or P4HB blend may be injection molded directly from a powder or granular form, however, in a preferred embodiment, the starting P4HB homopolymer or P4HB blend is extruded into pellets. Pellets of P4HB blends may be compounded by metering in the desired ratio of polymers into a single or twin-screw extruder, wherein they are mixed prior to being extruded into pellets. These pellets can then be used to produce molded compositions comprising P4HB using injection molding processes described herein. The molded compositions may either be used directly as biocompatible implants or further processed for use as, or in, a biocompatible implant.

In a particularly preferred embodiment, the pellets or granules suitable for injection molding that comprise P4HB have intrinsic viscosities ranging from 0.8 to 3.2 dl/g, and more preferably from 1.26 to 2.27 dl/g. In particular the intrinsic viscosity should not be less than 0.8 or greater than 3.2 dl/g.

BRIEF DESCRIPTION OF THE DRAWINGS

FIG. 1 shows the chemical structure of poly-4-hydroxybutyrate.

DETAILED DESCRIPTION OF THE INVENTION

I. Definitions

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Lexington, Mass.).

"Copolymers of poly-4-hydroxybutyrate" as generally used herein means any polymer comprising 4-hydroxybutyrate with one or more different hydroxy acid units.

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, hyaluronic acid and derivatives thereof, aptamers, siRNA, nucleic acids, and combinations thereof. "Bioactive agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer comprised of two or more different monomers.

"Molecular weight" as used herein, unless otherwise specified, refers to the weight average molecular weight (Mw), not the number average molecular weight (Mn), and is measured by GPC relative to polystyrene.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

II. Compositions

Methods have been developed to process P4HB compositions with intrinsic viscosities ranging from 0.8 to 3.2 dl/g into moldings. These moldings may be used as biocompatible implants, or may be converted to biocompatible implants through further processing.

A. P4HB Homopolymer

The processes described herein can typically be used with poly-4-hydroxybutyrate (P4HB). P4HB homopolymer can be obtained from Tepha, Inc. of Lexington, Mass., USA. The polymer may comprise the P4HB homopolymer blended with other absorbable polymers. Other absorbable polymers include, but are not limited to, poly(lactides); poly(glycolides); poly(lactide-co-glycolides); poly(lactic acid); poly (glycolic acid); poly(lactic acid-co-glycolic acids); polycaprolactones; poly(orthoesters); polyanhydrides; poly (phosphazenes); polyhydroxyalkanoates (including PHB, PHBV, and P4HB copolymers); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly (dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompabible or biodegradable polymers, for example, poly(lactide), poly(lactide-co-glycolide, or polycaprolactone or combinations thereof.

If desired, the compositions for injection molding may also incorporate reinforcing elements to improve the properties of the moldings. Such reinforcing elements may be used to improve properties such as tensile strength and resilience to shock. Ideally, the reinforcing elements have higher melting temperatures than P4HB so they retain their reinforcing properties during injection molding. In a preferred embodiment, the reinforcing elements are resorbable biocompatible fibers. In a particularly preferred embodiment, the reinforcing elements are fibers of polymers with monomers selected from glycolic acid, lactic acid, trimethylene carbonate, p-dioxanone, and ε-caprolactone.

The P4HB polymer or P4HB blend may be injection molded directly from a powder or granular form, however, in a preferred embodiment, the starting P4HB homopolymer or P4HB blend is extruded into pellets. Pellets of P4HB blends may be compounded by metering in the desired ratio of polymers into a single or twin-screw extruder, wherein they are mixed prior to being extruded into pellets. These pellets can then be used to produce molded compositions comprising P4HB using injection molding processes described herein. The molded compositions may either be used directly as biocompatible implants or further processed for use as, or in, a biocompatible implant.

In a particularly preferred embodiment, the pellets or granules suitable for injection molding that comprise P4HB have intrinsic viscosities ranging from 0.8 to 3.2 dl/g, and more preferably from 1.26 to 2.27 dl/g. In particular the intrinsic viscosity should not be less than 0.8 or greater than 3.2 dl/g. The intrinsic viscosity of the P4HB polymer may be determined using an Agilent 1100 Series HPLC equipped with an Agilent triple detector system (Agilent 390-LC Multi Detector Suite). The triple detector is equipped with a laser light scattering (LS) detector, a refractive index (RI) detector and a viscosity (Vis) detector. Samples of polymer may be prepared at 1 mg/ml in chloroform, and 100 μl of the solutions injected onto a Polymer Labs, PLgel column (5 micron, mixed C, 300×7.5 mm), and eluted at 1 ml/min. Intrinsic viscosity values may be determined using the Cirrus™ GPC/Multi Detector Software.

B. Incorporation of Additives into P4HB and Blends Thereof

Certain additives may be incorporated into the P4HB homopolymer and P4HB blends prior to injection molding. Preferably, these additives are incorporated during the compounding process to produce the pellets for injection molding. In a preferred embodiment, the additives are biocompatible, and even more preferably the additives are both biocompatible and resorbable.

In a preferred embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB homopolymer or P4HB blend. Such agents may be used to improve the mechanical properties of the moldings, and to reduce injection molding cycle times. Preferred nucleating agents include, but are not limited to, salts of acceptable organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl)dimerate, butyl ricinoleate, glyceryl tri-(acetyl ricinoleate), methyl ricinoleate, n-butyl acetyl ricinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers and radioactive substances. These additives may also be incorporated into the P4HB homopolymer and P4HB blend either before injection molding or afterwards.

C. Compounding of P4HB Polymer and Blends Thereof with Bioactive Agents

If desired, moldings made from P4HB homopolymer and blends of P4HB may incorporate bioactive agents. These agents may be added during the formulation process, during the pelletization process, or may be added later to the molding by coating or impregnating the moldings. If desired, the bioactive agents, the P4HB polymer or P4HB blend, may be dissolved in a solvent or solvent system in order to disperse the bioactive agent in the P4HB polymer or blend, and the solvent may then be removed by evaporation. Preferred solvents include methylene chloride, chloroform, dichloroethane, tetrachloroethane, trichloroethane, dibromomethane, bromoform, tetrahydrofuran, acetone, dimethylformamide, and 1,4-dioxane.

III. Methods of Injection Molding P4HB Homopolymer and Blends Thereof

To avoid significant loss of intrinsic viscosity during injection molding of P4HB and P4HB blends, it has been discovered that it is necessary to carefully dry the polymer(s) prior to molding. The specific extent of drying necessary depends on the loss of intrinsic viscosity that can be tolerated for a particular application. In a preferred embodiment, the polymer or blend to be injection molded is dried such that the moisture content of the polymer or blend is no greater than 0.5% by weight as measured gravimetrically, and more preferably no greater than 0.05% by weight. The polymer or blend may be dried in vacuo. In a particularly preferred method, the polymer or blend is dried in a vacuum chamber under a vacuum of at least 10 mbar, more preferably of at least 0.8 mbar, to a moisture content of less than 0.03% by weight. Elevated temperatures below the melting point of the polymer pellets may also be used in the drying process. Alternatively, the polymer may be dried by extraction into a solvent and re-precipitation, or with the use of desiccants.

The moisture content of samples including P4HB may be determined using a Vapor Pro Moisture Analyzer from Arizona Instruments, or similar instrument, as follows. Samples should be transferred to test vials in a low humidity environment (<5% RH) to minimize pickup of ambient moisture. Samples (1 g) can then be heated to 120° C. under a purge of dry nitrogen. The moisture content of the purge gas is determined by the Vapor Pro and reported as a % of the sample weight.

In a typical procedure for injection molding P4HB and P4HB blends, the injection molding process uses controlled processing conditions of temperature, time, speed, and pressure, wherein the dried pellets are melt processed, injected into a mold, cooled, and then molded. In one embodiment, a hydraulic injection molding machine with an 18 mm screw is started, and the temperatures are set for the heat zones (usually 4) to melt the polymer pellets, and for the mold. In a preferred embodiment where there are 4 heat zones, the heat zones are set as follows: zone 1 150-180° C., zone 2 170-190°

C., zone 3 180-220° C., and nozzle 180-220° C., and the mold temperature is set at 3-40° C. The extruder screw speed is also set at 20-400 rpm, and more preferably at 300 rpm. The polymer pellets are fed into the hopper of the injection molding extruder, and the screw conveys the polymer from the hopper down the length of the barrel, typically through a non-return valve, to the screw tip. The conveying action of the screw builds up pressure in front of its tip. This pressure pushes back the screw. As soon as there is enough supply of melt in the space for one shot, the rotation of the screw stops. At that time the nozzle has been pushed against the sprue bushing of the mold and the mold is clamped. Next a sudden controlled pressure surge in the hydraulic cylinder pushes the screw forward and pumps the melt into the mold cavity. In a preferred embodiment, the injection pressure is 750 psi (5.17 MPa) to 1250 psi (8.62 MPa), and more preferably 850 psi (5.86 MPa) to 1000 psi (6.89 MPa). This portion of the procedure represents the initial fill cycle where the mold is about 95% filled (by volume). The injection speed is set high enough to push the polymer into the mold, but not so high that it produces inadequate venting of the cavity to cause dieseling, jetting of the polymer into the cavity, or excessive molecular weight degradation. In a preferred embodiment, the injection speed is set in the range of 5 cm/sec to 20 cm/sec, and more preferably around 10 cm/sec. The shot size is set so that there is sufficient polymer to fill the mold, but not so large as to cause excessive flashings. The injection filling cycle is dependent upon the intrinsic viscosity of the polymer, and may be adjusted as desired by selection of the injection speed, polymer melt temperature, and mold temperature.

The packing/holding phase of the injection molding cycle begins after the mold filling phase. During the holding/packing phase, the molding machine forces 1% to 10% additional polymer (by volume) into the mold cavity. The cavity is held under pressure until the gate(s) in the mold freeze off such that no more polymer can enter the mold. The packing/holding pressure is typically set high enough in conjunction with enough time to allow the gate(s) to freeze to prevent voids and sink marks from forming, but low enough to prevent the formation of excess flashings. In a preferred embodiment, the holding pressure is 750 psi (5.17 MPa) to 1250 psi (8.62 MPa), and more preferably 850 psi (5.86 MPa) to 1000 psi (6.89 MPa). The holding time is also set so that there is sufficient time to allow the gates to freeze off without the formation of voids, sink marks as well as moldings with irregular dimensions. In a preferred embodiment, the holding time for this cycle is 2 to 8 seconds, and more preferably 3 to 5 seconds. At the end of the holding time when the molded parts are sufficiently solidified and cooled, the clamping unit is opened, and the molded parts in the mold half that is mounted on the movable platen are ejected. In a preferred embodiment, the cooling time is 60 to 150 seconds, and more preferably 90 to 120 seconds.

Preferred settings for a hydraulic injection molding of the P4HB homopolymer are shown in Table 1. One skilled in the art will recognize that the process is not limited to hydraulic injection molding machines, and that the moldings may also be made using electric, mechanical, and hybrid injection molding machines.

TABLE 1

Typical Settings for Injection Molding P4HB

| Injection Molding Settings | Range of Values |
| --- | --- |
| Zone 1 (° C.) | 150-200 |
| Zone 2 (° C.) | 150-200 |
| Zone 3 (° C.) | 150-225 |

TABLE 1-continued

Typical Settings for Injection Molding P4HB

| Injection Molding Settings | Range of Values |
| --- | --- |
| Nozzle (° C.) | 150-225 |
| Mold (° C.) Fixed Half | 28-35 |
| Mold (° C.) Movable Half | 28-35 |
| Injection Pressure (MPa) | 5.8-6.9 |
| Hold Pressure (MPa) | 5.8-6.9 |
| Hold Time (sec) | 5 |
| Cool Time (sec) | 90-120 |

It has also been discovered that the crystallinity content of the injection molded P4HB products can be increased by annealing of the molded products preferably at temperatures of 45-55° C., but not exceeding 60° C. In a preferred embodiment, the injection molded P4HB products are heated in a water bath. The ratio of crystallinity/amorphous content may also be manipulated by changing the retention time in the mold, the speed of cooling the mold, and by annealing the molded products in a post molding heat cycle.

IV. Fabrication of Implants from Moldings of P4HB Homopolymer and P4HB Blends

Implants made from moldings of P4HB polymer and P4HB blends, made by injection molding, have substantially improved properties for many medical applications relative to the same compositions made from brittle degradable thermoplastics. In particular, these implants have improved toughness that prevents breakage of the implant either during implantation or prior to the conclusion of healing.

The use of implants with lower intrinsic viscosities is particularly advantageous because the resorption time in vivo of these implants is faster than for implants having higher intrinsic viscosities. By careful selection of the intrinsic viscosity of starting P4HB polymer, and control of injection molding processing parameters, it is possible to produce implants with a range of different intrinsic viscosities, and therefore tailor the P4HB resorption rates to different applications. In an embodiment, implants with an intrinsic viscosity of less than 3.2 dl/g, but greater than 0.6 dl/g, are preferred.

Implants made from injection moldings comprising P4HB polymer, and blends comprising P4HB, may be used for soft and hard tissue repair, regeneration, and replacement. Implants made from injection moldings of P4HB polymer and P4HB blends may be used in the following medical devices, including but not limited to: suture anchors, screws, pins, including locking pins, bone plates, interference screws, tacks, nails, fasteners, rivets, staples, medullary cavity nails, clips, clamps, tubes, tissue engineering scaffolds, rotator cuff repair devices, meniscus repair devices, guided tissue repair/regeneration devices, articular cartilage repair devices, tendon repair devices, ligament repair devices, fixation devices for an implant, plastic surgery devices (including devices for fixation of facial and breast cosmetic and reconstructive devices), fixation devices for surgical meshes, facial reconstructive devices, spinal fusion devices, devices for treatment of osteoarthritis, imaging devices, and bone graft substitutes.

The present invention will be further understood by referenced to the following non-limiting examples.

Example 1

Pelletization of P4HB Homopolymer and Drying

P4HB granules with an intrinsic viscosity of 2.18 dl/g, and a moisture content no greater than 0.03% by weight after vacuum drying, were pelletized using a co-rotating fully intermeshing twin screw extruder with a screw diameter of 27 mm, length to diameter ratio of 40/1, screws rotating at 125-135 rpm, and with the barrel temperature of the extruder increasing from 100° C. at the feed zone to 210° C. at the die. The feed throat of the extruder was water cooled to 30° C. The P4HB granules were added directly to a loss-in-weight feeder, and fed to the extruder at a feed rate of 3.0 kg/hr. The extrudate was quenched immediately in cold water at 10° C., and once sufficiently cooled was cut into pellets using a pelletizer to yield P4HB pellets with an intrinsic viscosity of 2.01 dl/g. The loss of intrinsic viscosity on pelletization was 7.8%.

Example 2

Injection Molding of P4HB to Make Tensile Bar "Dog Bones"

Materials and Methods

Tensile bars "dog bones" were injection molded from P4HB homopolymer pellets prepared in Example 1 with an intrinsic viscosity of 2.01 dl/g, and water moisture content of less than 0.03% by weight (after vacuum drying), using an Arburg 221 Allrounder Model 25 Ton injection molding machine and the conditions specified in Table 2. The dog bone test samples had nominal dimensions of 2.5 inch (63.5 mm) length×0.125 inch (3.18 mm) width×0.062 inch (1.59 mm) thickness, and intrinsic viscosity of 1.99 dl/g representing a 1.0% loss of P4HB intrinsic viscosity during molding. Therefore, the total loss of intrinsic viscosity that resulted from pelletization and injection molding was 8.8% (7.8% for pelletization shown in Example 1 plus 1.0% for the injection molding step). For comparison, dog bones were also injection molded directly from P4HB granules with an intrinsic viscosity of 2.18 dl/g and moisture content of less than 0.03% by weight. Without an intermediate conversion to P4HB pellets, this yielded dog bones with an intrinsic viscosity of 2.05 dl/g representing a 6.0% loss of P4HB intrinsic viscosity.

TABLE 2

| Injection Molding Settings for Example 2 | |
| --- | --- |
| Zone 1 (° C.) | 170/169 |
| Zone 2 (° C.) | 190/193 |
| Zone 3 (° C.) | 200/194 |
| Zone 4 (° C.) | 200/202 |
| Screw speed rpm | 340 |
| Screw motor dosage B27 | 14.5 |
| Injection speed B29 | 19.5 |
| Injection retract stop B28 | 20.0 |
| Holding pressure B26 | 14.9/16.1 |
| Clamp close (s) | 2.5 |
| Clamp open (s) | 2.5 |
| Inject speed (s) | 5.0 |
| Injection pressure | 900 psi (6.2 N/mm$^2$) |
| Hold pressure | 900 psi (6.2 N/mm$^2$) |
| Back pressure | 400 psi (2.76 N/mm$^2$) |
| Injection delay time (s) | 1.3 |
| 1$^{st}$ stage time (s) | 2.2 |
| 2$^{nd}$ stage time (s) | 3.5 |
| Cool time (s) | 99.0 |
| Mold open time (s) | 3.0 |
| Mold Temp (° C.) | 32 |

Results

Tensile properties of the dog bone samples were determined in triplicate using a MTS test machine (Model: Insight 5, MTS Systems Corp., Eden Prarie, Minn.) with a 2 inch/min (5.08 cm/min) cross head speed. The tensile strength at break, percent elongation at break, and Young's modulus were determined according to methods known in the art, for example, ASTM D882-12 test method described in "Standard Test Method for Tensile Properties of Thin Plastic Sheeting". The MTS test machine was equipped with a 1,000 Newton load cell, grip separation of 2.54 cm, and a gage length of 7.62 mm. For each analysis, the dog bone test sample was stretched until breakage occurred, and a load-versus-extension plot was generated to determine the tensile strength at break, percent elongation at break, and elastic modulus properties. The tensile strength at break was calculated as the load at break divided by the cross-sectional area of the dog bone test sample, and is defined in units of mega-Pascal (MPa). The percent elongation at break was calculated by dividing (i) the length of the extension at the point of rupture, by (ii) the gauge length, and then multiplying by 100. Young's modulus was calculated as the slope of the initial linear portion of the load-extension curve, and is defined in units of MPa. The tensile properties of the P4HB dog bone samples are shown in Table 3.

TABLE 3

| Tensile properties of P4HB dog bones | | |
| --- | --- | --- |
| | Molded from P4HB Granules | Molded from P4HB Pellets |
| Intrinsic viscosity (dl/g) | 2.05 | 1.99 |
| Tensile Strength (N/mm2) | 33.6 | 31.7 |
| Young's Modulus (N/mm2) | 235.0 | 217.4 |
| Elongation at Break (%) | 254 | 210.1 |

Example 3

Injection Molding of a P4HB Orthopedic Pin

An orthopedic pin of 2 mm diameter and 70 mm length was injection molded from P4HB granules with an intrinsic viscosity of 2.35 dl/g, and water moisture content of less than 0.05% to yield an intrinsic viscosity of 2.30 dl/g with a customized Sodick Plustech 20 Ton Model 20EH2 injection molding machine. In this process the screw and barrel melted and conveyed the polymer to a plunger system. The screw and barrel ranged in temperature from 120° C. to 220° C. and had a screw speed of 30 rpm. The pool of polymer melt was then injected by the plunger at a speed of 50 mm/s and at a pressure of 2880 bar, into a mold under a clamping pressure of 15 tons. The polymer melt was subjected to a packing pressure of 2900 bar for 1.5 seconds and then a holding pressure of 1900 bar for 7.8 seconds. After the packing and holding phase the polymer was then held in a continuously cooled mold for 50 seconds at a temperature of 15° C. to solidify the polymer enough for it to be ejected from the mold without damage.

Example 4

Annealing of Injection Molded P4HB Orthopedic Pins

Injection molded orthopedic pins were heated for 24 hours at 45° C., 50° C., and 55° C., and their melting points determined with a differential scanning calorimeter (DSC). The melt temperatures ($T_m$) of the pins are shown in Table 4, and show a significant increase in the melt temperature as the annealing temperature is increased from 45° C. to 55° C. consistent with an increasing crystallinity of the pins.

TABLE 4

| Melt temperatures of annealed injection molded P4HB orthopedic pins | |
| --- | --- |
| Sample | Tm (° C.) |
| P4HB Pin- No annealing | 63.6 |
| P4HB Pin - Annealed at 45° C./24 hr | 65.6 |
| P4HB Pin - Annealed at 50° C./24 hr | 68.6 |
| P4HB Pin - Annealed at 55° C./24 hr | 76.3 |

We claim:

1. A process for producing moldings comprising poly-4-hydroxybutyrate the process comprising
feeding a poly-4-hydroxybutyrate (P4HB) polymer with an intrinsic viscosity between 0.8 and 3.2 dl/g, and a moisture content of less than 0.5% by weight, to an injection molding machine,
melting the polymer at a temperature of at least 150° C.,
injecting the melted polymer into a mold set at a temperature less than the melt temperature of the polymer under pressure effective to fill the mold, and
holding the polymer in the mold for a time period effective to form a molding.

2. The process of claim 1 wherein the intrinsic viscosity of the P4HB polymer decreases less than 25% upon molding.

3. The process of claim 1 wherein the intrinsic viscosity of the P4HB polymer decreases less than 10% upon molding.

4. The process of claim 1 wherein the molding is subsequently annealed at a temperature of less than 60° C.

5. The process of claim 4 wherein the melt temperature of the molding increases more than 1° C. upon annealing at 45° C.

6. The process of claim 4 wherein the melt temperature of the molding increases more than 4° C. upon annealing at 50° C.

7. The process of claim 4 wherein the melt temperature of the molding increases more than 10° C. upon annealing at 55° C.

8. A molding comprising P4HB produced by the processes of claim 1.

9. A medical device produced by the process of claim 1.

10. The device of claim 9 wherein the device is formed by machining the molding.

11. The device of claim 9 selected from the group consisting of suture anchors, screws, pins, including locking pins, bone plates, interference screws, tacks, nails, fasteners, rivets, staples, medullary cavity nails, clips, clamps, tubes, tissue engineering scaffolds, rotator cuff repair devices, meniscus repair devices, guided tissue repair/regeneration devices, articular cartilage repair devices, tendon repair devices, ligament repair devices, fixation devices for an implant, plastic surgery devices (including devices for fixation of facial and breast cosmetic and reconstructive devices), fixation devices for surgical meshes, facial reconstructive devices, spinal fusion devices, devices for treatment of osteoarthritis, imaging devices, and bone graft substitutes.

12. The device of claim 9 wherein the device further comprises a second polymer, nucleant, plasticizer, reinforcing element, bioactive agent, contrast agent, radiopaque marker and/or radioactive substance.

13. The device of claim 12 wherein the second polymer is a poly(lactide); poly(glycolide); poly(lactide-co-glycolide); poly(lactic acid); poly(glycolic acid); poly(lactic acid-co-glycolic acid); polycaprolactone; poly(orthoester); polyanhydride; poly(phosphazene); polyhydroxyalkanoates; poly-3-hydroxybutyrate; copolymer of 3-hydroxybutyrate with 3-hydroxyvalerate; P4HB copolymer; synthetically or biologically prepared polyester; polyester with one or more of the following monomeric units: glycolic, lactic; trimethylene carbonate, p-dioxanone, or $\epsilon$-caprolactone; poly(lactide-co-caprolactone); polycarbonate; tyrosine polycarbonate; polyamide; synthetic or natural polyamide, polypeptide, poly (amino acid); polyesteramide; poly(dioxanone); poly (alkylene alkylate); polyether; polyethylene glycol; polyethylene oxide; polyvinyl pyrrolidone; polyurethane; polyetherester; polyacetal; polycyanoacrylate; poly(oxyethylene)/poly(oxypropylene) copolymer; polyacetal, polyketal; polyphosphate; phosphorous-containing polymer; polyphosphoester; polyalkylene oxalate; polyalkylene succinate; poly(maleic acid); chitin; chitosan; modified chitosan; hyaluronic acid and derivatives thereof; hydrophilic or water soluble polymer.

14. The device of claim 9 wherein the device is used for the repair, regeneration, or replacement of soft or hard tissues.

* * * * *